United States Patent [19]

Eglington

[11] 4,444,783
[45] Apr. 24, 1984

[54] β-LACTAM ANTIBACTERIAL AGENTS, A PROCESS FOR THE PREPARATION AND USE IN PHARMACEUTICAL COMPOSITIONS

[75] Inventor: Alfred J. Eglington, Betchworth, England

[73] Assignee: Beecham Group Limited, England

[21] Appl. No.: 307,630

[22] Filed: Oct. 1, 1981

Related U.S. Application Data

[63] Continuation of Ser. No. 59,314, Jul. 20, 1979, abandoned.

[30] Foreign Application Priority Data

Aug. 2, 1978 [GB] United Kingdom ............... 31991/78
Aug. 25, 1978 [GB] United Kingdom ............... 43581/78

[51] Int. Cl.³ .................... C07D 487/04; A61K 31/40
[52] U.S. Cl. ............................. 424/274; 260/245.2 T; 424/114
[58] Field of Search ................. 260/245.2 T; 424/274

[56] References Cited

U.S. PATENT DOCUMENTS 3,926,955 12/1975 Burton et al. .
4,146,610 3/1979 Cole et al. ................... 260/245.2 T
4,162,323 7/1979 Kahan ......................... 260/245.2 T
4,172,129 10/1979 Cole et al. ................... 260/245.2 T
4,229,443 10/1980 Binderup .
4,231,928 11/1980 Naito et al. .
4,237,051 12/1980 McCombie .
4,244,965 1/1981 Howarth et al. .
4,246,262 1/1981 Vangedal .
4,252,722 2/1981 Melillo et al. .
4,278,686 7/1981 Corbett et al. .

FOREIGN PATENT DOCUMENTS 2356649 1/1978 France .

Primary Examiner—Mary C. Lee
Attorney, Agent, or Firm—Jacobs & Jacobs

[57] ABSTRACT

The compounds of the formulaes (IV), (V) and (VI):

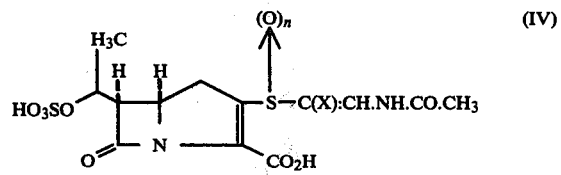

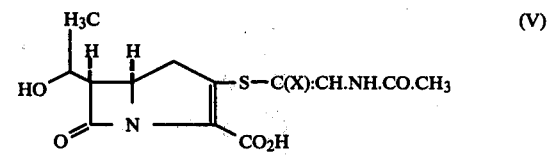

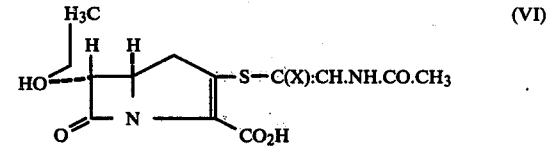

and salts and esters thereof where X is a bromine or chlorine atom, and n is 0 or 1; are antibacterial agents. Their preparation and use is described.

77 Claims, No Drawings

β-LACTAM ANTIBACTERIAL AGENTS, A PROCESS FOR THE PREPARATION AND USE IN PHARMACEUTICAL COMPOSITIONS

This is a continuation of Ser. No. 059,314 filed July 20, 1979 now abandoned.

The compounds of Formulae (I), (II) and (III):

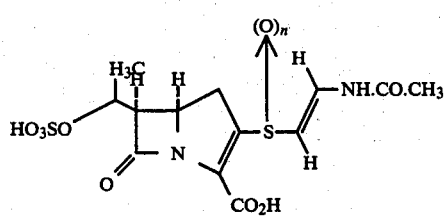

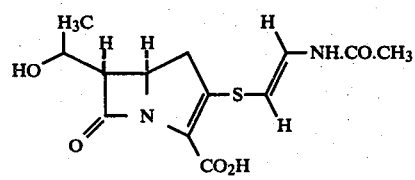

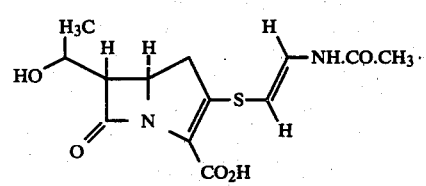

wherein n is 0 or 1
and their salts have been described in British Pat. No. 1 489 235 and Belgian Pat. No. 827332 Derivatives wherein a halogen atom is introduced into the Sidechain have been found to be β-lactamase inhibitors and to have antibacterial activity.

The present invention provides the compounds of the formulae (IV), (V) and (VI):

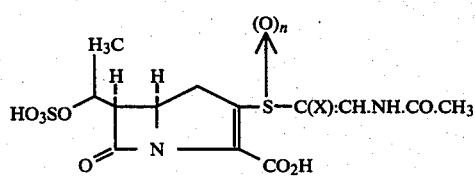

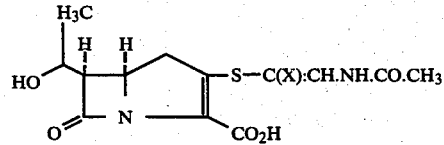

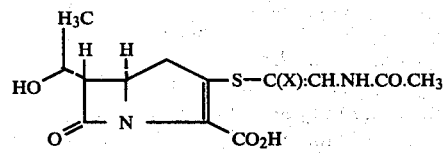

and salts and esters thereof where X is a bromine or chlorine atom, and n is 0 or 1.

The compounds of the formulae (IV), (V) and (VI) and their salts and esters may have the E- or Z-stereochemistry about the double bond or may be provided as mixtures of compounds having these stereochemistries.

Suitably n is 1 in the compound of formula (IV). More suitably n is 0 in the compound of formula (IV).

Suitably X is bromine. Suitably X is chlorine.

Favourably the compounds of the formula (IV) are in the form of a pharmaceutically acceptble di-basic salt such as the di-sodium, di-potassium or like salt. Alternatively, the compounds of the formula (IV) are in the form of a mono-basic pharmaceutically acceptable salt of an in-vivo hydrolysable carboxylate ester such as the sodium or potassium sulphate salt of the phthalidyl or like carboxylate ester.

Favourably the compounds of the formula (V) and (VI) are in the form of a pharmaceutically acceptable salt such as the sodium or potassium salt. Alternatively the compounds of the formula (V) and (VI) are in the form of an in-vivo hydrolysable ester such as the phthalidyl or like ester.

Other esters of the above compounds which are worthy of mention include those such as the p-nitrobenzyl ester which serve as intermediates.

Diesters of the compounds of the formula (IV) are also useful intermediates, for example the ethyl sulphate ester of p-nitrobenzyl carboxylate ester.

The present invention also provides a pharmaceutical composition which comprises a compound of this invention and a pharmaceutically acceptable carrier.

Such compositions may be formulated in conventional manner, for example as described for a compound of the formula (I), (II) or (III). Favourably the compositions are in unit dosage form containing 25–500 mg of the active compound. Such compositions may be administered from 2 to 4 times a day to susceptible gram-positive or gram-negative bacteria such as strains of *Staphylococcus aureus, Klebsiella aerogenes, Escherichia coli* and the like. Administration of such compositions may be by injection or per os.

The compounds of this invention are also able to enhance the effectiveness of penicillins and cephalosporins against β-lactamase producing strains of gram-positive and gram-negative bacteria presumably by virtue of being β-lactamase inhibitors. Thus this invention also provides pharmaceutical compositions as described above which also comprise a penicillin or cephalosporin. Suitable penicillins include ampicillin and amoxycillin, for example as their trihydrates or sodium salts. Suitable cephalosporins include cephaloridine and sodium cefazolin. Generally the weight ratio of compound of this invention to penicillin or cephalosporin is from 10:1 to 1:10 and more usually from 1:1 to 1:5.

In a further aspect the present invention provides a process for the preparation of a compound of the formula (IV), (V) or (VI) or salt or ester which process comprises the reaction of a compound of the formula (I), (II) or (III) as a salt or ester thereof with $X_2$ where X is as defined in relation to formulae (IV), (V) and (VI) and a base.

The reaction is most suitably carried out in an inert organic solvent such as dichloromethane at a depressed temperature such as −70° C. The base used should be soluble in the reaction mixture so it is usual to use an organic tertiary amine such as triethylamine or 2,6-lutidine.

Since the reaction takes place in an organic solvent if a salt of the compound of the formula (IV) (V) or (VI) is employed this is most suitably a salt of a lipophilic amine, for example the benzyldimethyl-n-hexadecylammonium salt. Such salts may be preformed or formed in situ from an alternative salt such as the sodium salt in conventional manner.

If cleavable esters of the compounds of the formula (IV), (V) or (VI) are employed these may also be converted into corresponding salts if desired in known manner.

The compounds of this invention may be purified chromatographically, for example by using column chromatography or high pressure liquid chromatography. A suitable chromatographic support for purification of esters is silica gel. Suitable chromatographic supports for purification of the salts of the compounds of formula (IV), (V) or (VI) are Biogel P-2, Amberlite XAD-4, DIAION HP20 and the like.

The following Examples illustrate this invention

EXAMPLE 1

Methyl (5R,6R)-3-(2-acetamido-1-bromoethenylthio)-6-[(1S)-1-ethoxysulphonyloxyethyl]-7-oxo-1-azabicyclo[3.2.0-]hept-2-ene-2-carboxylate Methyl (5R,6R)-3-[(E)-2-acetamidoethenylthio]-6-[(1S)-1-ethoxysulphonyloxy-ethyl]-7-oxo-1-azabicyclo[3.2.0]hept-2-ene-2-carboxylate (110 mg) in dry dichloromethane (4 ml) was cooled to $-70°$ (acetone/solid $CO_2$ bath) and bromine (0.25 ml of a 1 M solution in $CCl_4$) was added to the stirred solution. After 20 mins, triethylamine (50 mg) in dichloromethane (0.5 ml) was added and stirring was continued at $-70°$ for 15 min. The mixture was allowed to warm to room temperature over 30 min. The solution was then washed with water (2×), dried ($MgSO_4$) and evaporated in vacuo to give a brown oil (130 mg). This was chromatographed on silica gel (10 g; 230–430 mesh ASTM) eluting with ethyl acetate/cyclohexane (8:2) to give, after combination and evaporation of the appropriate fractions, methyl (5R,6R)-3-(2-acetamido-1-bromoethylthio)-6-[(1S)-1-ethoxysulphonyloxyethyl]-7-oxo-1-azabicyclo[3.2.0]hept-2-ene-2-carboxylate (39 mg), $\lambda_{max}$ (EtOH), 310 and 245 nm, $\nu_{max}$ ($CH_2Cl_2$) 1790, 1720, 1625 cm$^{-1}$, $\delta(CDCl_3)$ 1.40 (3H, t, J 7 Hz, $CH_3CH$), 2.12 (3H, s, $CH_3CO$), 3.07 (1H,dd, $J_1$ 19 Hz, $J_2$ 10 Hz 4-$CH_AH_BCH$), 3.39 (1H,dd, $J_1$ 19 Hz, $J_2$ 9.5 Hz, 4-$CH_AH_BCH$), 3.7–3.9 (4H, s, at $\delta$ 3.80 superposed on m, $OCH_3$ 6-$CH$), 4.1.–4.5 (3H, q, J 7 Hz at 4.30, superposed on m, $OCH_2CH_3$, 5-$CH$) 4.7–5.2 (1H,m, $CH.CH.CH_3$), 7.42 (1H, broad d, J 11.5 Hz, $CONHCH$), 7.70 (1H, d, J 11.5 Hz,=$CHNHCO$).

EXAMPLE 2

Benzyl (5R,6R)-3-(2-acetamido-1-bromoethenylthio)-6-[(1S)-1-ethoxysulphonyloxyethyl]-7-oxo-1-azabicyclo[3.2.0.-]hept-2-ene-2-carboxylate Benzyl (5R,6R)-3-[(E)-2-acetamidoethenylthio]-6-[(1S)-1-ethoxy-sulphonyloxyethyl]-7-oxo-1-azabicyclo[3.2.0.]hept-2-ene-2-carboxylate (ca. 70 mg) in dichloromethane (2 ml) was cooled in an acetone/solid $CO_2$ bath and an M/1 solution of bromine in carbon tetrachloride (0.1 ml) was added. After 30 min. methanol (1 ml), followed by triethylamine (0.2 ml of a 100 mg/ml solution in dichloromethane), was added. The mixture was stirred in the cold for 1 hr. and then dichloromethane (10 ml) was added and the mixture was allowed to warm to room temperature. Water (5 ml) was then added and the mixture was shaken and separated. The dichloromethane layer was dried ($MgSO_4$) and evaporated in vacuo. The residue was chromatographed on silica gel (9 g: 230–400 mesh ASTM) eluting with ethyl acetate/cyclohexane mixtures (8:2, then 9:1 and finally EtOAc). This gave benzyl (5R,6R)-3-(2-acetamido-1-bromoethenylthio)-6-[(1S)-1-ethoxysulphonyloxyethyl]-7-oxo-1-azabicyclo[3.2.0.]hept-2-ene-2-carboxylate (15 mg), 243 nm, $\lambda_{max}$ (EtOH) 311 and 243 nm, $\delta$ ($CDCl_3$)1.38 (3H, t, J 7 Hz, $CH_3CH_2$), 1.63 (3H, d, J 6 Hz, $CH_3CH$), 2.10 (3H, s, $CH_3CO$), 3.06 (1H, dd, $J_1$ 19 Hz, $J_2$ 10 Hz, 4-$CH_AH_BCH$), 3.37 (1H, dd, $J_1$ 19 Hz, $J_2$ 9.5 Hz, 4-$CH_AH_BCH$), 3.76 (1H, dd $J_1$ 10 Hz, $J_2$ 6 Hz, $J_2$ 6 Hz, 6-$CH$), 4.0–4.5 (m, 3H, 5-$CH$, $OCH_2CH_3$), 4.7–5.1 (1H, m, $CH.CHCH_3$), 5.22. (2H, s, $CH_2Ar$), 7.1–7.5 (ca. 6H, m, 5×Ar-H, NH) 7.66 (1H, d, J 11.5 Hz, $NHCH$=C).$\nu_{max}$ ($CH_2Cl_2$) 1785, 1715, 1620, 1200 cm$^{-1}$.

EXAMPLE 3 p-Nitrobenzyl (5R,6R)-3-(2-acetamido-1-bromoethenylthio)-6-[benzyldimethyl-n-hexadecylammonium (1S)-1-sulphonatooxyethyl]-7-oxo-1-azabicyclo[3.2.0.-]hept-2-ene-2-carboxylate p-Nitrobenzyl (5R,6R)-3-[(E)-2-acetamidoethenylthio]-6-[sodium (1S)-1-sulphonatooxyethyl]-7-oxo-1-azabicyclo[3.2.0.]hept-2-ene-2-carboxylate (158 mg) in water (10 ml) was shaken with a solution of benzyldimethyl-n-hexadecylammonium chloride (115 mg) in dichloromethane (10 ml). The layers were separated and the dichloromethane layer was dried ($MgSO_4$) and then evaporated in vacuo to give the quaternary ammonium salt as a gum. This was taken up in dry dichloromethane (5 ml), cooled to $-70°$ and treated with bromine (0.46 ml of a 100 mg/ml solution in $CCl_4$). The mixture was stirred in the cold for 15 min. and the triethylamine (30 mg) in dichloromethane (1 ml) was added. After stirring for a further fifteen minutes the temperature was allowed to warm to ambient and the mixture was stirred for a further 30 min. The mixture was washed with water, dried ($MgSO_4$) and evaporated in vacuo to leave p-nitrobenzyl (5R,6R)-3-[2-acetamido-1-bromoethenylthio)-6-(benzyldimethyl-n-hexadecylammonium (1S)-1-sulphonatooxyethyl]-7-oxo-1-azabicyclo[3.2.0.]hept-2-ene-2-carboxylate as a gum, $\nu_{max}$ 1780, 1710, 1625 cm$^{-1}$.

EXAMPLE 4 p-Nitrobenzyl (5R,6R)-3-(2-acetamido-1-bromoethenylthio)-6-[sodium-(1S)-1-sulphonatooxyethyl]-7-oxo-1-azabicyclo[3.2.0.]-hept-2-ene-2-carboxylate p-Nitrobenzyl (5R,6R)-3-[(E)-2-acetamidoethenylthio]-6-[sodium-(1S)-1-sulphonatooxyethyl]-7-oxo-1-azabicyclo[3.2.0.]hept-2-ene-2-carboxylate (100 mg) in water and benzyldimethyl-n-hexadecylammonium chloride in dichloromethane were shaken together, the layers separated and the dichloromethane layer was dried ($MgSO_4$) and evaporated in vacuo to give the monoester quaternary-ammonium salt. This was taken up in dry dichloromethane (3 ml) and treated with 1.1 equivalents of triethyloxonium tetrafluoroborate. The mixture was stirred for 3 hr., to give a solution of the diester. This solution was cooled to $-70°$ (acetone/solid $CO_2$ bath) and 2,6-lutidine (0.2 ml), followed by methanol (0.5 ml), was added. A solution of bromine (1 equivalent) in carbon tetrachloride was then added and the mixture was then allowed to warm to room temperature. The mixture was chromatographed on silica gel (10 g) eluting with ethyl acetate/petroleum ether (b.p. 60°–80°) mixtures; 8:2 (25 ml); 9:2 and then with ethylacetate, combination and evaporation in vacuo of the requisite fractions yielded p-nitrobenzyl (5R,6R)-3-(2-acetamido-1-bromoethylthio)-6-[(1S)-1-ethoxysulphonyloxyethyl]-7-oxo-1-azabicyclo[3.2.0.]hept-2-ene-2-carboxylate (33 mg), m.p. 131°–141°; $[\alpha]_D^{20}$ −80.9° (c 1% CHCl$_3$), $\lambda_{max}$(EtOH) 317 ($\epsilon$max 14,200) and 255 ($\epsilon$max 19,400) nm; $\nu$max (CH$_2$Cl$_2$) 1785, 1720, 1625 cm$^{-1}$, $\delta$(CDCl$_3$) 1.41 (3H, t, J 6 Hz, CH$_3$CH$_2$), 1.66 (3H, d, J 6 Hz, CH$_3$CH), 2.14 (3H, s, CH$_3$CO), 3.10 (1H, dd, J 18 and 11 Hz, 4-CH$_A$H$_B$CH), 3.43 (1H, dd, J 18 and 9 Hz, 4-CH$_A$H$_B$CH), 3.82 (1H, dd, J 6 and 11 Hz, 6-CH), 4.1–4.5 (3H, m, CH$_2$CH$_3$, 5-CH), 4.8–5.2 (1H, m, CH$_3$CHCH), 5.28 and 5.45 (2H, AB$_q$, J 18 Hz, OCH$_2$Ar), 7.2–7.8 (4H, m, 2×Ar-H, NH, C=CH); 8.15 (2H, d, J 9 Hz, 2×Ar-H). (Found: C, 42.0; H, 3.6; N, 6.5; Br, 12.5. C$_{22}$H$_{24}$BrN$_3$O$_{10}$S$_2$ requires C, 41.6; H, 3.8; N, 6.6; Br, 12.6%).

The diester was taken up in N,N-dimethylformamide (1 ml) and treated with sodium iodide (7.6 mg) and the mixture stirred at room temperature for 2 h. The mixture was then warmed to 50°–60° for 1 hr. and then more sodium iodide (2 mg) was added and heating was continued for a further 30 mins. The mixture was then cooled and evaporated in vacuo and chromatographed on silica gel (10 g) eluting with chloroform (5 ml), followed by chloroform/ethanol mixtures using a gradient elution. Collection, combination and evaporation in vacuo of the requisite fractions gave p-nitrobenzyl (5R,6R)-3-(2-acetamido-1-bromo-ethenylthio)-6-[sodium (1S)-1-sulphonatooxyethyl]-7-oxo-1-azabicyclo[3.2.0.]hept-2-ene-2-carboxylate; $\lambda_{max}$ (H$_2$O) 311, 252 (inf), 229. $\nu_{max}$ (KBr) 1775, 1690, 1620 cm$^{-1}$.

EXAMPLE 5

Disodium (5R,6R)-3-(2-acetamido-1-bromoethenylthio)-6-[(1S)-1-sulphonatooxyethyl]-7-oxo-1-azabicyclo[3.2.0.]hept-2-ene-2-carboxylate Disodium (5R,6R)-3-[(E)-2-acetamidoethenylthio]-6-[(1S)-1-sulphonatooxyethyl]-7-oxo-1-azabicyclo[3.2.0.]hept-2-ene-2-carboxylate (100 mg) in water (10 ml) was treated with benzyldimethyl-n-hexadecylammonium chloride (180 mg) in dichloromethane (10 ml). After shaking the mixture was separated and the dichloromethane layer was dried (MgSO$_4$) and evaporated in vacuo to leave the diquaternary ammonium salt. This was taken up in dry dichloromethane (5 ml), cooled to −70° (acetone/solid CO$_2$ bath) and a solution of bromine in carbon tetrachloride (0.38 ml 100 mg/ml) was added. The mixture was stirred for 5 min. and then triethylamine (1 eq.) was added. The mixture was warmed to room temperature, diluted with CH$_2$Cl$_2$ (8 ml) and then washed with water (5 ml). The dichloromethane layer was then extracted with water (2 ml) containing sodium tetrafluoroborate (100 mg) and the resultant aqueous extract was placed on a Biogel P-2 column (8×3 cm) and eluted with water. Fractions containing 3 to 5 ml of H$_2$O were collected. Fractions 17–21 showed the expected chromophore. Fractions 22ff showed end absorption, suggesting they contaned inorganic impurities. Fractions 17–21 were combined and evaporated in vacuo to low volume (ca 3 ml) and ethanol (15 ml) was added and evaporated in vacuo to low volume (3×), then ethanol was added and evaporated in vacuo to dryness (ZX), then toluene (15 ml) was added to the residue and evaporated in vacuo to leave disodium (5R,6R)-3-(2-acetamido-1-bromoethenylthio)-6-[(1S)-1-sulphonatooxyethyl]-7-oxo-1-azabicyclo[3.2.0.]hept-2-ene-2-carboxylate as a colourless solid, $\lambda$max (H$_2$O) 298 and 250 nm; $\nu_{max}$ (KBr) 1750, 1690, 1620 cm$^{-1}$.

EXAMPLE 6 p-Bromobenzyl (5R,6R)-3-(2-acetamido-1-chloroethenylthio)-6-[(1S)-1-ethyloxysulphonyloxyethyl]-7-oxo-1-azabicyclo[3.2.0.]hept-2-ene-2-carboxylate p-Bromobenzyl (5R,6R)-3-[(E)-2-acetamidoethenylthio]-6-[sodium(1S)-1-sulphonatooxyethyl]-7-oxo-1-azabicyclo[3.2.0.]hept-2-ene-2-carboxylate (150 mg) was suspended in dry dichloro methane (4 ml) and treated with triethyloxonium tetrafluoroborate (0.5 ml of a 100 mg/ml solution in CH$_2$Cl$_2$). The mixture was stirred for 30 min., diluted to 10 ml and treated with H$_2$O (5 ml) and saturated aqueous sodium chloride (5 ml). The mixture was shaken and separated, the CH$_2$Cl$_2$ layer was dried (MgSO$_4$) and evaporated in vacuo to leave the diester as an oil (52 mg). This was taken up in dry dichloromethane (2 ml), cooled to −70° (acetone/solid CO$_2$ bath) and treated with a freshly prepared solution of chlorine in carbon tetrachloride (0.2 ml; 35 mg/ml). After stirring for 5 min. at −70° triethylamine (0.1 ml of a 100 mg/ml solution in CH$_2$Cl$_2$) was added and stirring was continued for a further 10 min. The mixture was then allowed to warm to room temperature, loaded onto a silica gel column, and eluted with ethyl acetate/cyclohexane (8:2) to give p-bromobenzyl (5R,6R)-3-(2-acetamido-1-chloroethenylthio)-6-[(1S)-1-ethyloxysulphonyloxyethyl]-7-oxo-1-azabicyclo[3.2.0.]hept-2-ene-2-carboxylate (26 mg), $\lambda_{max}$ (EtOH) 310 nm, $\nu_{max}$(CH$_2$Cl$_2$) 1785, 1710, 1630 cm$^{-1}$.

EXAMPLE 7

Disodium (5R,6R)-3-(2-acetamido-1-chloroethenylthio)-6-[(1S)-1-sulphonatooxyethyl]-7-oxo-1-azabicyclo[3.2.0.]hept-2-ene-2-carboxylate

Method I

Di(benzyldimethyl-n-hexadecylammonium) (5R,6R)-3-[(E)-2-acetamidoethenylthio]-6-[(1S)-1-sulphonatooxyethyl]-7-oxo-1-azabicyclo[3.2.0.]hept-2-ene-2-carboxylate was prepared from the corresponding disodium salt (200 mg) by an analogous manner to that described in Example 5, and dissolved in dichloromethane (4 ml), cooled to −70° (acetone/solid CO$_2$ bath) and treated with a solution of chlorine in CCl$_4$ (0.78 ml of 41.3 mg/ml solution), followed after 1 min. by triethylamine in dichloromethane (0.46 ml; 100 mg/ml solution).

The mixture was stirred in the cold for 30 min., warmed to room temperature to give a solution of the diquaternary ammonium salt in CH$_2$Cl$_2$. This was washed with water, followed by NaBF$_4$ (300 mg) in H$_2$O (2 ml). The aqueous layer from the aqueous NaBF$_4$ wash was adjusted to pH 7 using dilute aqueous NaHCO$_3$ and loaded onto a Biogel P2 column (ca. 18×3 cm) and the column was eluted with deionised H$_2$O/1% nBuOH, the pH of which had been adjusted to 7.0. 5 to 10 ml fractions were collected and monitored by u.v. Fractions 9 and 10 showed a u.v. chromophore with an inflexion ca. 285 nm and a maximum at 247 nm. These were considered to contain the chlorocompound disodium salt. These fractions were evaporated in vacuo, ethanol (5 ml) was added and evaporated in vacuo (3×), and toluene (5 ml) was added evaporated in vacuo to give a solid (103 mg). The i.r. indicated that this was NaBF$_4$ together with a quantity of the required chloro-compound. The estimated purity of this preparation was not greater than 20% (u.v. $\lambda_{max}$248, $\epsilon_{max}$1,980).

Method II

The procedure for the preparation of the diquaternary ammonium salt of the chloro-compound in CH$_2$Cl$_2$ as described in method I was repeated. This was washed with water (2 ml) and then the CH$_2$Cl$_2$ solution was extracted with sodium iodide (500 mg) in aqueous 5% NaCl (6 ml), to give an aqueous solution of the disodium salt of the chloro-compound mixed with NaCl and NaI. Desalting was achieved by loading the foregoing solution onto an Amberlite XAD-4 column (13×2.3 cm). The column was eluted with 5% aqueous NaCl and then with deionised water collecting ca 5 ml fractions. Fractions 26–36 contained low concentrations of the disodium salt. (u.v. assay). These fractions were combined and evaporated in vacuo to low volume. Ethanol (10 ml) was added and evaporated in vacuo (3×) to low volume, and on the final evaporation to dryness. Toluene was added to the residue and evaporated in vacuo (3×) to give the required disodium salt. U.V. assay indicated that only a little degradation had occurred in the evaporation sequence.

EXAMPLE 8

Disodium (5R,6R)-3-(2-acetamido-1-bromoethenylthio)-6-[(1S)-1-sulphonatooxyethyl]-7-oxo-1-azabicyclo[3.2.0]hept-2-ene-2-carboxylate

Method A

Disodium (5R,6R)-3-[(E)-2-acetamidoethenylthio]-6-[(1S)-1-sulphonatooxyethyl]-7-oxo-1-azabicyclo[3.2.0]hept-2-ene-2-carboxylate (100 mg) in water (10 ml) was treated with benzyldimethyl-n-hexadecylammonium chloride (180 mg) in dichloromethane (10 ml). After shaking the mixture was separated and the dichloromethane layer was dried (MgSO$_4$) and evaporated in vacuo to leave the diquaternary ammonium salt. This was taken up in dry CH$_2$Cl$_2$ (5 ml), cooled to −70° (acetone/solid CO$_2$ bath) and a solution of bromine in CCl$_4$ (0.38 ml 100 mg/ml) was added. The mixture was stirred for 5 min and then triethylamine (1 equivalent) in CH$_2$Cl$_2$ was added. The mixture was allowed to warm to room temperature, diluted with CH$_2$Cl$_2$ (8 ml) and then washed with water (5 ml). The dichloromethane layer was then extracted with a 5% solution of NaCl in water (5 ml) containing sodium iodide (150 mg). This extract was loaded on to an Amberlite X AD-4 Column (3×15 cm) and eluted with 5% NaCl in H$_2$O, followed by H$_2$O (100 ml), followed by 5% n-propanol in water, and finally by 10% n-propanol in water. The 5% propanol fractions contained the desired compound (v.v. assay) and the requisite fractions were combined and evaporated in vacuo to low volume. Ethanol (15 ml) was added and evaporated in vacuo to low volume (ca 3 ml) (2×), and then ethanol (15 ml) was added and evaporated in vacuo to dryness. Toluene (15 ml) was added to the residue and evaporated in vacuo to dryness (2×) to give disodium (5R,6R)-3-(2-acetamido-1-bromethenylthio)-6-[(1S)-1-sulphonatooxyethyl]-7-oxo-1-azabicyclo[3.2.0]hept-2-ene-2-carboxylate (17 mg).

Method B

Method A was repeated except in the workup the dichloromethane layer was extracted with a 5% solution of NaCl in water (3 ml) containing sodium iodide (150 mg). This extract was loaded onto a DIAION HP20 column (19×1 cm; ca. 15–20 ml of resin) and eluted with 5% NaCl in H$_2$O (50 ml); then with 2% NaCl in H$_2$O (20 ml) and finally with deionised water. The deionised water eluate contained the bromo-derivative (u.v. assay) and the requisite fractions were combined and evaporated in vacuo to low volume. Ethanol was then added and evaporated in vacuo to low volume (several times) and then ethanol was added the mixture triturated and then the ethanol was evaporated in vacuo to dryness. Toluene was added to the residue was triturated, and the toluene was evaporated in vacuo to dryness (2×) to leave disodium (5R,6R)-3-(2-acetamido-1-bromoethenylthio)-6-[(1S)-1-sulphonatooxyethyl]-7-oxo-1-azabicyclo[3.2.0]hept-2-ene-2-carboxylate (39 mg), $\lambda$max (H$_2$O) 299 ($\epsilon_{max}$ 10,000), 250(12,500) nm.

EXAMPLE 9 p-Nitrobenzyl (5R,6R)-3-(2-acetamido-1-chloroethenylthio)-6-[(1S)-1-ethoxysulphonyloxyethyl]-7-oxo-1-azabicyclo[3.2.0]hept-2-ene-2-carboxylate p-Nitrobenzyl (5R,6R)-3-[(E)-2-acetamidoethenylthio]-6-[sodium (1S)-1-sulphonatooxyethyl]-7-oxo-1-azabicyclo-[3.2.0]hept-2-ene-2-carboxylate (100 mg) in water (5 ml) was treated with benzyldimethyl-n-hexadecylammonium chloride (73 mg) in CH$_2$Cl$_2$ (5 ml). On shaking an emulsion formed, this was dispersed by addition of an aqueous NaCl solution. The layers were separated and the CH$_2$Cl$_2$ layer was dried (MgSO$_4$) and evaporated in vacuo to give the quaternary ammonium salt. This was taken up in dry CH$_2$Cl$_2$ (4 ml) and treated with a solution of triethyloxonium tetrafluoroborate in CH$_2$Cl$_2$ (0.35 ml; 100 mg/ml). After 30 min t.l.c. indicated that the diester had formed. The solution was cooled (solid CO$_2$/industrial methylated spirits bath) and a freshly prepared solution of Cl$_2$ in CH$_2$Cl$_2$ (0.26 ml; 25 mg/ml) was added. After 5 min triethylamine in CH$_2$Cl$_2$ (0.18 ml; 100 mg/ml) was added and the mixture was allowed to warm to room temperature. The mixture was then washed with water, dried (MgSO$_4$) and evaporated in vacuo. The residue was chromatographed on silica gel (230–400 mesh ASTM) (8 g) eluting with ethyl acetate/cyclohexane mixtures; 8:2 (25 ml); 9:1 (25 ml); EtOAc. Fractions containing the chloro-compound were combined and evaporated to give p-nitrobenzyl (5R,6R)-3-(2-acetamido-1-chloroethenylthio)-6-[(1S)-1-ethoxysulphonatooxyethyl]-7-oxo-1-azabicyclo[3.2.0]hept-2-ene-2-carboxylate (48 mg) as on oil which partially crystallised on standing. $\lambda$max(EtOH) 307, 260 nm. $\nu$max (CH$_2$Cl$_2$) 1790, 1715, 1730 cm$^{-1}$.

EXAMPLE 10

Methyl (5R,6R)-3-(2-acetamido-1-bromoethenylsulphinyl)-6-[benzyldimethyl-n-hexadecylammonium (1S)-1-sulphonatooxyethyl]-7-oxo-1-azabicyclo[3.2.0]hept-2-ene-2-carboxylate Methyl (5R,6R),-3-[(ε)-2-acetamidoethenylsulphinyl]-6-[sodium (1S)-1-sulphonatooxyethyl]-7-oxo-1-azabicyclo[3.2.0]hept-2-ene-2-carboxylate (40 mg) in $(CD_3)_2SO$ (0.4 ml) was treated with $CH_2Cl_2$ (10 ml) containing benzyldimethyl-n-hexadecylammonium chloride (36 mg) and with water (10 ml). After shaking the layers were separated and the $CH_2Cl_2$ layer was washed with water (5 ml) dried ($MgSO_4$), and evaporated in vacuo. The residue was taken up in dry $CH_2Cl_2$ (4 ml), cooled to $-70°$ (solid $CO_2$/EtOH bath) and bromine in $CCl_4$ (0.15 ml; 100 mg/ml) was added. After 5 mins triethylamine in $CH_2Cl_2$ (0.11 ml; 100 mg/ml) was added and the solution was allowed to warm to room temperature. The solution was diluted with $CH_2Cl_2$ (10 ml), washed with water, dried ($MgSO_4$) and evaporated in vacuo to leave methyl (5R,6R)-3-(2-acetamido-1-bromoethenylsulphinyl)-6-[benzyldimethyl-n-hexadecylammonium (1S)-1-sulphonatooxyethyl]-7-oxo-1-azabicyclo[3.2.0]hept-2-ene-2-carboxylate as an oil, λmax ($CH_2Cl_2$) 1790, 1725, 1625 cm$^{-1}$, δ($CDCl_3$) (inter alia) 8.08 (1H, d, J ca 11 Hz, C(Cl):CH.NH), 8.66 (1H, broad d, J Ca 11 Hz, CH.NHCO) ppm.

EXAMPLE 11 p-Nitrobenzyl (5R,6S)-3-(2-acetamido-1-bromoethenylthio)-6-[(S)-1-hydroxyethyl]-7-oxo-1-azabicyclo[3.2.0]hept-2-ene-2-carboxylate p-Nitrobenzyl (5R,6S)-3-[(E)-2-acetamidoethenylthio]-6-[(1S)-1-hydroxyethyl]-7-oxo-1-azabicyclo[hept-2-ene-2-carboxylate (100 mg) in N,N-dimethylformamide (2 ml) was cooled to $-30°$ and a solution of bromine in carbon tetrachloride (0.36 ml; 100 mg/ml) was added. After stirring for 2–3 minutes, triethylamine in dichloromethane (0.22 ml; 100 mg/ml) was added and stirring in the cold was continued for 10 minutes. The mixture was allowed to warm to room temperature and the dimethylformamide was removed by evaporation in vacuo. Ethyl acetate (15 ml) and water (20 ml) were added to the residue and after separation the ethyl acetate layer was washed with water (15 ml), saturated brine, dried ($MgSO_4$) and evaporated in vacuo. The residue was chromatographed on silica gel (230–400 mesh ASTM) (12 g), eluting with ethyl acetate to give (the second potassium permanganate oxidisable material as monitored by t.l.c.) the title compound (21 mg) as a ca 3:1 mixture of double bond isomers: λ$_{max}$(EtOH) 318 (10.100), 253 (20,400); λ$_{max}$ ($CH_2Cl_2$) 1780, 1715, 1615 cm$^{-1}$; δ($CDCl_3$) (Major isomer) 1.36 (3H, d, J 6 Hz), 2.15 (3H, s), 2.8–3.6 (3H, m), 4.0–4.4 (2H, m), 5.23 and 5.50 (2H, ABq, J 15 Hz), 7.3–7.9 (4H, m), 8.22 (2H, d, J 9 Hz).

EXAMPLE 12

Sodium (5R,6S)-3-(2-acetamido-1-bromoethenylthio)-6-[(S)-1-hydroxyethyl]-7-oxo-1-azabicyclo[3.2.0]hept-2-ene-2-carboxylate Sodium (5R,6S)-3-[(E)-2-acetamidoethenylthio]-6-[(S)-1-hydroxyethyl]-7-oxo-1-azabicyclo[3.2.0]hept-2-ene-2-carboxylate (200 mg of 52.6% pure material) in water (10 ml) was treated with Aliquat 336 (500 mg) in dichloromethane (10 ml). After separation the aqueous solution was re-extracted with dichloromethane (10 ml) containing Aliquat 336 (500 mg). The dichloromethane extracts were combined, dried ($MgSO_4$) and evaporated in vacuo to leave a mixture of Aliquat 336 and the quaternary ammonium salt corresponding to the starting sodium salt. This mixture was redissolved in dichloromethane (8 ml) cooled to $-70°$ and bromine in carbon tetrachloride (0.50 ml; 100 mg/ml) was added, followed by tiethylamine in dichloromethane (0.30 ml; 100 mg/ml). The mixture was allowed to warm to room temperature, the dichloromethane solution was washed with water (3.5 ml) and extracted with a saturated aqueous solution of NaCl(2×3.5 ml). The sodium chloride extracts were combined and loaded onto a DIAION HP20 column (8×1 cm) and the column eluted with saturated aqueous sodium chloride (10 ml) followed by deionised water. Fractions of the aqueous eluate were monitored by u.v. spectroscopy, and those containing a maximum in absorption at ca 300 nm were combined and evaporated in vacuo to low volume. Ethanol (ca 20 ml) was added and evaporated in vacuo to low volume (5×), on the last evaporation all the solvent was removed. Toluene was added to the residue and evaporated in vacuo (2×) to leave the title compound as a solid (24 mg):λmax ($H_2O$)246(11,300), and 297(8,800 nm). λmax(KBr) 1755, 1680, 1620 cm$^{-1}$.

EXAMPLE 13

Sodium (5R,6R)-3-(2-acetamido-1-bromoethenylthio)-6-[(S)-1-hydroxyethyl]-7-oxo-azabicyclo[3.2.0]hept-2-ene-2-carboxylate Sodium (5R,6R)-3-[(E)-2-acetamidoethenylthio]-6-[(S)-1-hydroxyethyl]-7-oxo-1-azabicyclo[3.2.0]hept-2-ene-2-carboxylate (200 mg; 85% pure) in water (10 ml) was treated with dichloromethane (10 ml) containing Aliquat 336 (600 mg). After shaking and separating the aqueous layer was again treated with dichloromethane (10 ml) containing Aliquat 336 (600 mg). The two dichloromethane extracts were dried ($MgSO_4$) and evaporated to leave a mixture of Aliquat 336 and the quaternary ammonium salt corresponding to the starting sodium salt. This mixture was taken up in dry dichloromethane (10 ml), cooled to $-70°$ and treated with triethylamine in dichloromethane (0.55 ml; 100 mg/ml), followed by bromine in carbon tetrachloride (0.82 ml; 100 mg/ml). After stirring in the cold for 25 minutes the mixture was warmed to room temperature, washed with water (3.5 ml) and extracted with saturated aqueous NaCl (2×5 ml). The NaCl extracts were combined and loaded onto a column of DIAION HP20 (18×1 cm). The column was eluted with saturated aqueous NaCl (25 ml) and then with deionised water. Some fractions containing the title compound (λmax ca 299 and 248 nm) were obtained. The column was then eluted with water containing 10% ethanol to give further fractions containing the title compound. Fractions containing the title compound were combined and evaporated in vacuo to low volume, ethanol was added and evaporated to low volume (4×), and toluene added and evaporated to dryness (3×) to give the title compound (29 mg) of estimated purity of ca 40%:λmax (H$_2$O) 300(6,100), 246 (9,000) nm; λmax(KBr) 1750, 1690, 1620 cm$^{-1}$.

EXAMPLE 14

Phthalidyl (5R,6R)-3-(2-acetamido-1-bromoethenylthio)-6-[sodium(1S)-1-sulphonato-oxyethyl]-7-oxo-1-azabicyclo[3.2.0]hept-2-ene-2-carboxylate Disodium (5R,6R)-3-(2-acetamido-1-bromoethenylthio)-6-[(1S)-1-sulphonato-oxythyl]-7-oxo-1-azabicyclo[3.2.0]hept-2-ene-2-carboxylate (210 mg; mixture of double bond isomers) in DMF (5 ml) was stirred with a mixture of 3 A and 4 A molecular sieves for 15 minutes and then bromophthalide (100 mg) was added. The mixture was stirred for 3 hours, the DMF was then removed by evaporation in vacuo, and the residue was suspended in chloroform (10 ml) and loaded onto a column of silica gel (20 g; 230–400 mesh ASTM). The column was eluted with chloroform (10 ml) and then with chloroform/ethanol mixtures; 7:3 (100 ml), followed by 6:4. The fractions was monitored by t.l.c. (silica gel; CHCl$_3$/EtOH 3:2 elution), and two distinct groups of fractions containing the title compound were obtained. Each group of fractions was combined and evaporated; yielding two components as solids:component (1) (125 mg):λmax 320(εmax 10,000), 236 (17,400) nm ν(KBr) 1780, 1710, 1610 cm$^{-1}$ and component (2) (64 mg): λmax 321 (εmax 11,400), 236 (18,800) nm. νmax (KBr) 1780, 1705, 1620 cm$^{-1}$.

EXAMPLE 15

Disodium (5R,6R)-3-(2-Acetamido-1-bromoethenylthio)-6-[(1S)-1-sulphonato-oxyethyl]-7-oxo-1-azabicyclo[3.2.0]hept-2-ene-2-carboxylate; Isomer I Disodium (5R,6R)-3-[(E)-2-acetamidoethenylthio]-6-[(1S)-1-sulphonato-oxyethyl]-7-oxo-1-azabicyclo[3.2.0]hept-2-ene-2-carboxylate (0.6 g; 80–85% pure) in water (25 ml) was extracted with dichloromethane containing benzyldimethyl-n-hexadecylammonium chloride (1.4 g). The aqueous solution was then re-extracted with dichloromethane containing benzyldimethyl-n-hexadecylammonium chloride (0.2 g). The dichloromethane extract were combined, dried (MgSO$_4$) and the solvent evaporated in vacuo. Toluene (30 ml) was added to the residue and evaporated in vacuo.

The residual diquaternary ammonium salt corresponding to the starting material was taken up in dry dichloromethane (40 ml), cooled to −70°, and treated with a solution of bromine in CCl$_4$ (2.2 ml; 100 mg/ml) which had been diluted to 5 ml with dichloromethane. The mixture was stirred at −70° for 3 minutes and triethylamine (160 mg) was added. After stirring at −70° for 15 minutes the mixture was warmed to room temperature, washed with water (10 ml) and extracted with an aqueous solution (15 ml) containing 5% w/v NaCl and sodium iodide (750 mg). The aqueous extract was loaded onto a (previously used) column of DI-AION HP20 (particle size 63–75 μm) (3.0×19.0 cm) and the column was eluted with an aqueous solution containg 5% w/v NaCl (100 ml) followed by deionised water. Fractions were monitored by u.v. and h.p.l.c. Fractions containing u.v. maxima at ca 298 and 246 nm and a peak with a retention time of ca 2.4 min on h.p.l.c. [Waters μ Bondapak C$_{18}$ Reverse Phase column; elution with pH 4.7 0.05 M NH$_4$H$_2$PO$_4$ aqueous solution containing 10% acetonitrile 2 ml/min] were combined and evaporated in vacuo to low volume, ethanol (20 ml) was added and evaporated in vacuo to low volume (3×) and then toluene (20 ml) was added and evaporated in vacuo to dryness (3×) to give the first isomer of disodium (5R,6R)-3-(2-acetamido-1-bromoethenylthio)-6-[(1S)-1-sulphonato-oxyethyl]-7-oxo-1-azabicyclo[3.2.0]hept-2-ene-2-carboxylate (151 mg):λmax (H$_2$O) 298 (12,700), 246 (15,200) nm; λmax (KBr) 1755, 1690, 1620, 1600(sh) cm$^{-1}$; δ(D$_2$O, relative to HOD at 4.63 ppm) 1.51 (3H, d, J 6 Hz), 2.15 (3H, s), 3.06 (1H, dd of ABX J$_1$ 18 Hz, J$_2$ 9 Hz), 3.46 (1H, dd of ABX, J, 18 Hz, J$_2$ 9 Hz), 3.86 (1H, dd, J, 9 Hz, J$_2$ 6 Hz), 4.1–4.5 (1H, m), 4.7–5.0 (1H, m), 7.68 (1H, s).

EXAMPLE 16

Disodium (5R,6R)-3-(2-Acetamido-1-bromoethenylthio)-6-[(1S)-1-sulphonato-oxyethyl]-7-oxo-1-azabicyclo[3.2.0]hept-2-ene-2-carboxylate; Isomer II Disodium (5R,6R)-3-[(E)-2-acetamidoethenylthio]-6-[(1S)-1-sulphonato-oxyethyl]-7-oxo-1-azabicyclo[3.2.0]hept-2-ene-2-carboxylate (1.2 g; 80–85% pure) in water (50 ml) was extracted with dichloromethane (50 ml) containing benzyldimethyl-n-hexadecylammonium chloride (2.6 g). The aqueous solution was re-extracted with dichloromethane (10 ml) containing benzyldimethyl-n-hexadecylammonium chloride (0.4 g). The dichloromethane extracts were combined, dried (MgSO), and evaporated in vacuo. Toluene (30 ml) was added to the residue and evaporated in vacuo. The residue was taken up in dry dichloromethane (70 ml), cooled to −70° and bromine in CCl$_4$ (4.3 ml; 100 mg/ml) was added. After 5 minutes triethylamine (300 mg) was added and the mixture was allowed to warm to ambient temperature and allowed to stand for 45 minutes. The mixture was extracted with an aqueous solution (15 ml) containing 5% w/v NaCl and NaI(1.5 g) and then re-extracted with an aqueous solution (10 ml) containing 5% w/v NaCl and sodium iodide (0.5 g). The combined extracts were loaded onto a column of (previously used) DI-AION HP20 (particle size 63 to 75 μm) (3.0×19.0 cm) and eluted with an aqueous solution containing 5% w/v NaCl (150 ml), deionised water (400 ml) and then with water containing 10% ethanol. The second isomer was eluted with aqueous ethanol. Fractions containing the second isomer λmax ca 295, 255 nm, h.p.l.c. retention time ca 4.2 min using the system described in EXAMPLE 15) were combined and evaporated in vacuo and the residue was further purified by redissolving in an aqueous solution containing 5% w/v NaCl (7 ml), the pH was adjusted to 7.1 and the resultant solution was loaded onto a column of previously unused DIAION HP 20 (63–75 μm) (3.0×19.0 cm) and the column eluted with an aqueous solution containing 5% w/v NaCl (20 ml) followed by deionised water. Fractions containing isomer II were combined, the pH adjusted to 7.1 and the solvent evaporated in vacuo to low volume, ethanol (20 ml) was added and evaporated to low volume (3×) and then toluene was added and evaporated to dryness (3×) to give the second isomer of disodium (5R,6R)-3-(2-acetamido-1-bromoethenylthio)-6-[1S-sulphonatooxyethyl]-7-oxo-1-azabicyclo[3.2.0]hept-2-ene-2-carboxylate (121 mg):λmax (H$_2$O) 294 (10,900), 253 (14,200) nm; λmax (KBr) 1755, 1690, 1610 cm$^{-1}$, δ(D$_2$O, signals relative to HOD at δ4.56 ppm) 1.41 (3H, d, J 6 Hz), 3.00 (1H, dd of ABX, J$_1$ 19 Hz, J$_2$ 9.5 Hz) 3.35 (1H, dd of ABX, J$_1$ 19 Hz, J$_2$ 9 Hz), 3.79 (1H, dd, J$_1$ 9 Hz), J$_2$ 6 Hz) 4.1–4.5 (1H, m), 4.6–4.9 (1H, m), 7.65 (1H, s).

EXAMPLE 17 p-Nitrobenzyl (5R,6R)-3-(2-acetamido-1-bromoethenylthio)-6-[sodium(1S)-1-sulphonato-oxyethyl]-7-oxo-1-azabicyclo[3.2.0]hept-2-ene-2-carboxylate; Isomers I and II Disodium (5R,6R)-3-(2-acetamido-1-bromoethenylthio)-6-[(1S)-sulphonato-oxyethyl]-7-oxo-1-azabicyclo[3.2.0]hept-2-ene-2-carboxylate (250 mg; mixture of double bond isomers) in N,N-dimethylformamide (8 ml) was treated with p-nitrobenzyl bromide (250 mg) for 2 hours. The solvent was removed by evaporation in vacuo, the residue was suspended in chloroform and loaded onto a column of silica gel (25 g; 1:1 mixture of particle size 0.040–0.063 mm and particle size less than 0.063 mm). The column was eluted with 10% EtOH in CHCl$_3$ (100 ml), then with 20% EtOH in CHCl$_3$ (100 ml) and then with 30% EtOH in CHCl$_3$. The first β-lactam containing component to be eluted was a single isomer of the title compound (50 mg) contaminated by some degradation products, λmax(KBr) 1775, 1690, 1610 cm$^{-1}$. Crystals deposited from the latter fractions. These were filtered off and dried to give the more polar isomer of the title compound (76 mg) mp. 179°–183° dec.; λmax(H$_2$O) 252 (21,400), 311 (16,100) nm; λmax(KBr) 1775, 1690, 1620 cm$^{-1}$; δ[(CD$_3$)$_2$ NCDO], 1.47 (3H, d, J 5.8 Hz), 2.16 (3H, s), 3.13 (1H, dd of ABX, J$_1$ 19.4 Hz, J$_2$ 10.2 Hz) 3.83 (1H, dd of ABX, J$_1$ 19.4 Hz, J$_2$ 8.8 Hz), 3.80 (1H, dd J$_1$ 10.6 Hz, J$_2$ 5.7 Hz), 4.2–4.8 (2H, m) 5.35 and 5.58 (2H, ABq, J 14 Hz), 7.75 (1H, d, J 10.8 Hz), 7.83 (2H, d, J 9 Hz), 8.39 (2H, d, J 9 Hz), 10.00 (1H, d, J 10.8 Hz). Evaporation of the mother liquors yielded a further 116 mg of the more polar isomer of the title compound.

EXAMPLE 18

Disodium (5R,6R)-3-(2-acetamido-1-bromoethenylthio)-6-[(1S)-1-sulphonato-oxyethyl]-7-1-azabicyclo[3.2.0]hept-2-ene-2-carboxylate; Isomer I p-Nitrobenzyl (5R,6R)-3-(2-acetamido-1-bromoethenylthio)-6-[sodium(1S)-1-sulphonato-oxyethyl]-7-oxo-1-azabicyclo[3.2.0]hept-2-ene-2-carboxylate (the more polar isomer from example 17, 20 mg) was added to a suspension of prehydrogenated (15 mins.) 5% Pd/C catalyst in dioxan containing 30% water (10 ml). The mixture was hydrogenated for 4 hours, the catalyst was filtered off and sodium hydrogen carbonate (5 mg) added to the filtrate. The dioxan was partially removed by evaporation in vacuo, water (10 ml) added and the mixture washed with ethyl acetate (10 ml). The aqueous solution was evaporated to low volume and loaded onto a column of Biogel P-2 (2.0×7.0 cm) and the column eluted with water to give the title compound, identical by h.p.l.c. to the isomer I prepared in Example 15.

EXAMPLE 19

Disodium (5R,6R)-3-(2-acetamido-1-bromoethenylthio)-6-[(1S)-1-sulphonato-oxyethyl]-7-oxo-1-azabicyclo[3.2.0]hept-2-ene-2-carboxylate; Isomer II p-Nitrobenzyl (5R,6R)-3-(2-acetamido-1-bromoethenylthio)-6-[sodium(1S)-1-sulphonato-oxyethyl]-7-oxo-1-azabicyclo[3.2.0]hept-2-ene-2-carboxylate (the less polar isomer from example 17, 20 mg), was hydrogenated in an analogous manner to that described in example 18, to give after work-up as as in example 18, the title compound identical by h.p.l.c. to the isomer II prepared in example 16.

Demonstration of Effectiveness (a) the MICs (DST agar containing 10% v/v horse blood) of the compound of Example 5 were determined by serial dilution. The following results were obtained:

|  | µg/ml |
|---|---|
| Citrobacter freundii E8 | 2.5 |
| Enterobacter cloacae N1 | 1.0 |
| Escherichia coli JT2OR+ | 1.0 |
| Klebsiella aerogenes A | 0.2 |
| Proteus mirabilis C977 | 0.5 |
| Proteus vulgaris WO91 | 0.2 |
| Pseudomonas aerogenosa A | 10 |
| Staphylococcus aureus Russel | 1.0 |

(b) When tested against a mouse intraperitoneal infection due to Escherichia coli 8 (dosing sub cutaneously 1, 1.5, 2 and 2.5 hours post infection) the compound of Example 5 was found to have a CD$_{50}$ of 32 mg/kg (the disodium salt of the compound of formula (I) also had a CD$_{50}$ of 32 mg/kg in this test).

(c) The MIC's (DST agar containing 10% v/v horseblood) of the compounds of Examples 13 and 14 were determined by serial dilution.

| ORGANISM | Compound of Example 13 AGAR | Component 2 (slower running) of Example 14 AGAR |
|---|---|---|
| Citrobacter freundii E8 | 12.5 | >50 |
| Enterobacter cloacae N1 | 0.2 | 5.0 |
| Escherichia coli 0111 | 0.8 | 5.0 |
| Escherichia coli JT 39 | 12.5 | 2.5 |
| Klebsiella aerogenes A | 0.8 | 0.2 |
| Proteus mirabilis C977 | 1.6 | 1.2 |
| Proteus morganii I580 | 12.5 | 1.2 |
| Proteus rettgeri WM16 | 25 | 12.5 |
| Proteus vulgaris WO91 | 25 | 12.5 |
| Pseudomonas aeruginosa A | >100 | >50 |
| Salmonella typhimurium CT10 | 0.8 | 1.2 |
| Serratia marcescens US 20 | 12.5 | 12.5 |
| Shigella sonnei MB 11967 | 0.8 | 1.2 |
| Bacillus subtilis A | ≦0.1 | 0.2 |
| Staphylococcus aureus Oxford | 0.4 | 1.2 |
| Staphylococcus aureus Russell | 0.8 | 1.2 |
| Staphylococcus aureus 1517 | 3.1 | >50 |
| Streptococcus faecalis I | 3.1 | >50 | inoculum 0.001 ml of a 10$^{-2}$ dilution for Gm+ve bacteria or a 10$^{-4}$ dilution for GM−ve organisms.

(d) The MICs (DST agar containing 5% v/v horse blood) of the compounds of Examples 15 and 16 were determined by serial dilution.

| Organism | Example 15 | Example 16 |
|---|---|---|
| E. cloacae N1 | 5.0 | >100 |
| E. coli 0111 | 2.5 | 25 |
| JT39 | 2.5 | 25 |
| ESS | 0.2 | 2.5 |
| K. aerogenes A | 0.2 | 10 |
| P. mirabilis 977 | 0.5 | 25 |
| P. morganii 1580 | 0.5 | 50 |
| P. rettgeri WM16 | 10 | >100 |
| P. vulgaris WO91 | 10 | >100 |
| P. aeruginosa A | >100 | >100 |
| S. typhimirium CT | 1.0 | 50 |
| S. marcescens US20 | 10 | >100 |
| S. Sennei MB11967 | 1.0 | 50 |
| B. subtilis A | 0.1 | 2.5 |
| S. aureus Oxford | 0.5 | 5.0 |
| Russell | 0.5 | 5.0 |
| 1517 | 100 | 100 |
| S. faecalis I | 25 | 100 |

*Serial dilution in DST agar containing 5% horse blood, inoculum 0.001 ml undiluted overnight broth culture.

What we claim is:

1. A compound of the formula (IV)

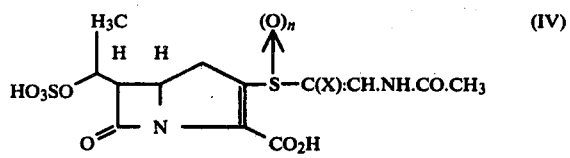

a pharmaceutically acceptable salt thereof, a cleavable ester thereof or a pharmaceutically acceptable salt of a cleavable ester thereof wherein X is bromo or chloro and n is 0 or 1.

2. A compound according to claim 1 of the formula (IV) in the form of a pharmaceutically acceptable dibasic salt.

3. A compound according to claim 1 having a single stereochemical form about the double bond.

4. A compound according to claim 1 wherein X is bromo.

5. A compound according to claim 1 wherein X is chloro.

6. A compound according to claim 1 of the formula (IV) wherein n is 1.

7. A compound according to claim 1 wherein n is 0.

8. A compound according to claim 2 in the form of the di-sodium salt.

9. A compound according to claim 2 in the form of the di-potassium salt.

10. A compound according to claim 1 of the formula (IV) in the form of a monobasic pharmaceutically acceptable salt of an in-vivo hydrolyzable carboxylate ester.

11. A compound according to claim 10 in the form of the sodium or potassium sulfonate salt of a phthalidyl ester.

12. The compound according to claim 1 which is Methyl (5R, 6R)-3-(2-Acetamido-1-bromoethenylthio)-6-[(1S)-1-ethoxysulphonyloxyethyl]-7-oxo-1-azabicyclo[3.2.0]hept-2-ene-2-carboxylate.

13. The compound according to claim 1 which is Benzyl (5R,6R)-3-(2-acetamido-1-bromoethenylthio)-6-[(1S)-1-ethoxysulphonyloxy-ethyl]-7-oxo-1-azabicyclo[3.2.0]hept-2-ene-2-carboxylate.

14. The compound according to claim 1 which is p-Nitrobenzyl (5R,6R)-3-(2-acetamido-1-bromoethenylthio)-6-[benzyldimethyl-n-hexadecylammonium (1S)-1-sulphonatooxyethyl]-7-oxo-1-azabicyclo [3.2.0]hept-2-ene-2-carboxylate.

15. The compound according to claim 1 which is p-Nitrobenzyl (5R, 6R)-3-(2-acetamido-1-bromoethenylthio)-6-[sodium-(1S)-1-sulphonatooxyethyl]-7-oxo-1-azabicyclo [3.2.0.]-hept-2-ene-2-carboxylate.

16. The compound according to claim 1 which is Disodium (5R, 6R)-3-(2-acetamido-1-bromoethenylthio)-6-[(1S)-1-sulphonatooxyethyl]-7-oxo-1-azabicyclo [3.2.0]hept-2-ene-2-carboxylate.

17. The compound according to claim 1 which is p-Bromobenzyl (5R,6R)-3-(2-acetamido-1-chloroethenylthio)-6-[(1S)-1-ethyloxysulphonyloxyethyl]-7-oxo-1-azabicyclo [3.2.0]hept-2-ene-2-carboxylate.

18. The compound according to claim 1 which is Disodium (5R, 6R)-3-(2-acetamido-1-chloroethenylthio)-6-[(1S)-1-sulphonatooxyethyl]-7-oxo-1-azabicyclo [3.2.0]hept-2-ene-2-carboxylate.

19. The compound according to claim 1 which is Disodium (5R, 6R)-3-(2-acetamido-1-bromoethenylthio)-6-[(1S)-1-sulphonatooxyethyl]-7-oxo-1-azabicyclo[3.2.0]hept-2-ene-2-carboxylate.

20. The compound according to claim 1 which is p-Nitrobenzyl (5R, 6R)-3-(2-acetamido-1-chloroethenylthio)-6-[(1S)-1-ethoxysulphonyloxyethyl]-7-oxo-1-azabicyclo[3.2.0.] hept-2-ene-2-carboxylate.

21. The compound according to claim 1 which is Methyl (5R,6R)-3-(2-acetamido-1-bromoethenylsulphinyl)-6-[benzyldimethyl-n-hexadecylammonium (1S)-1-sulphonatooxyethyl]-7-oxo-1-azabicyclo[3.2.0.]hept-2-ene-2-carboxylate.

22. The compound according to claim 1 which is Phthalidyl (5R,6R)-3-(2-acetamido-1-bromoethenylthio)-6-[sodium (1S)-1-sulphonato-oxyethyl]-7-oxo-1-azabicyclo-[3.2.0]hept-2-ene-2-carboxylate.

23. The compound according to claim 1 which is Disodium (5R,6R)-3-(2-acetamido-1-bromoethenylthio)-6-[(1S)-1-sulphonato-oxyethyl]-7-oxo-1-azabicyclo[3.2.0]hept-2-ene-2-carboxylate.

24. The compound according to claim 1 which is p-Nitrobenzyl (5R,6R)-3-(2-acetamido-1-bromoethenylthio)-6-[sodium (1S)-1-sulphonato-oxyethyl]-7-oxo-1-azabicyclo[3.2.0]hept-2-ene-2-carboxylate.

25. A pharmaceutical composition useful for treating bacterial infections in humans and animals which comprises an antibacterially effective amount of a compound of the formula (IV):

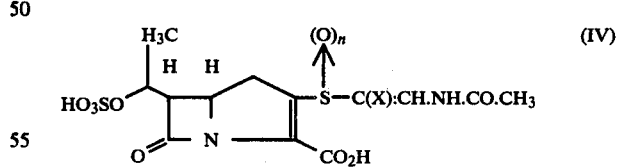

a pharmaceutically acceptable salt thereof, a cleavable ester thereof or a pharmaceutically acceptable salt of a cleavable ester thereof wherein X is bromo or chloro and n is 0 or 1, in combination with a pharmaceutically acceptable carrier.

26. A composition according to claim 25 wherein the compound is of the formula (IV) in the form of a pharmaceutically acceptable di-basic salt.

27. A composition according to claim 25 wherein the compound has a single stereochemical form about the double bond.

28. A composition according to claim 25 wherein X is bromo.

29. A composition according to claim 25 wherein X is chloro.

30. A composition according to claim 25 wherein the compound is of the formula (IV) wherein n is 1.

31. A composition according to claim 25 wherein the compound is of the formula (IV) wherein n is 0.

32. A composition according to claim 26 wherein the compound is in the form of the di-sodium salt.

33. A composition according to claim 26 wherein the compound is in the form of the di-potassium salt.

34. A composition according to claim 25 wherein the compound is of the formula (IV) in the form of a monobasic pharmaceutically acceptable salt of an in-vivo hydrolyzable carboxylate ester.

35. A composition according to claim 34 wherein the compound is in the form of the sodium or potassium sulfonate salt of the phthalidyl ester.

36. A composition according to claim 34 wherein the compound is Methyl (5R, 6R)-3-(2-Acetamido-1-bromoethenylthio)-6-[(1S)-1-ethoxysulphonyloxyethyl]-7-oxo-1-azabicyclo[3.2.0]hept-2-ene-2-carboxylate.

37. A composition according to claim 34 wherein the compound is Benzyl (5R, 6R)-3-(2-acetamido-1-bromoethenylthio)-6-[(1S)-1-ethoxysulphonyloxy-ethyl]-7-oxo-1-azabicyclo[3.2.0.]hept-2-ene-2-carboxylate.

38. A composition according to claim 34 wherein the compound is p-Nitrobenzyl (5R, 6R)-3-(2-acetamido-1-bromoethenylthio)-6-[benzyldimethyl-n-hexadecylammonium (1S)-1-sulphonatooxyethyl]-7-oxo-1-azabicyclo [3.2.0.]hept-2-ene-2-carboxylate.

39. A composition according to claim 25 wherein the compound is p-Nitrobenzyl (5R, 6R)-3-(2-acetamido-1-bromoethenylthio)-6-[sodium-(1S)-1-sulphonatooxyethyl]-7-oxo-1-azabicyclo [3.2.0.]-hept-2-ene-2-carboxylate.

40. A composition according to claim 25 wherein the compound is Disodium (5R, 6R)-3-(2-acetamido-1-bromoethenylthio)-6-[(1S)-1-sulphonatooxyethyl]-7-oxo-1-azabicyclo [3.2.0.]hept-2-ene-2-carboxylate.

41. A composition according to claim 25 wherein the compound is p-romobenzyl (5R, 6R)-3-(2-acetamido-1-chloroethenylthio)-6-[(1S)-1-ethyloxysulphonyloxy-ethyl]-7-oxo-1-azabicyclo [3.2.0.] hept-2-ene-2-carboxylate.

42. A composition according to claim 25 wherein the compound is Disodium (5R, 6R)-3-(2-acetamido-1-chloroethenylthio)-6-[(1S)-1-sulphonatooxyethyl]-7-oxo-1-azabicyclo [3.2.0.]hept-2-ene-2-carboxylate.

43. A composition according to claim 25 wherein the compound is Disodium (5R, 6R)-3-(2-acetamido-1-bromoethenylthio)-6-[(1S)-1-sulphonatooxyethyl]-7-oxo-1-azabicyclo[3.2.0]hept-2-ene-2-carboxylate.

44. A composition according to claim 25 wherein the compound is p-Nitrobenzyl (5R, 6R)-3-(2-acetamido-1-chloroethenylthio) 6-[(1S)-1-ethoxysulphonyloxyethyl]-7-oxo-1-azabicyclo[3.2.0.] hept-2-ene-2-carboxylate.

45. A composition according to claim 25 wherein the compound is Methyl (5R,6R)-3-(2-acetamido-1-bromoethenylsulphinyl)-6-[benzyldimethyl-n-hexadecylammonium (1S)-1-sulphonatooxyethyl]-7-oxo-1-azabicyclo[3.2.0.]hept-2-ene-2-carboxylate.

46. A composition according to claim 25 wherein the compound is Phthalidyl (5R,6R)-3-(2-acetamido-1-bromoethenylthio)-6-[sodium (1S)-1-sulphonato-oxyethyl]-7-oxo-1-azabicyclo-[3.2.0]hept-2-ene-2carboxylate.

47. A composition according to claim 25 wherein the compound is Disodium (5R,6R)-3-(2-acetamido-1-bromoethenylthio)-6-[(1S)-1-sulphonato-oxyethyl]-7-oxo-1-azabicyclo[3.2.0]hept-2-ene-2-carboxylate.

48. A composition according to claim 25 wherein the compound is p-Nitrobenzyl (5R,6R)-3-(2-acetamido-1-bromoethenylthio)-6-[sodium (1S)-1-sulphonato-oxyethyl]-7-oxo-1-azabicyclo[3.2.0]hept-2-ene-2-carboxylate.

49. A composition according to claim 25 in oral administration form.

50. A composition according to claim 25 in a form suitable for injection.

51. A method of treating bacterial infections in humans and animals which comprises administering to a human or animal in need thereof an antibacterially effective amount of a compound of the formula (IV), $$\begin{array}{c} H_3C \quad H \quad H \quad (O)_n \\ HO_3SO \quad \diagdown \quad \diagup \quad \uparrow \\ \quad \quad \quad \quad S-C(X):CH.NH.CO.CH_3 \\ O \quad N \quad CO_2H \end{array} \quad (IV)$$

a pharmaceutically acceptable salt, an in-vivo hydrolyzable ester thereof or a pharmaceutically acceptable salt of an in-vivo hydrolyzable ester thereof wherein X is bromo or chloro and n is 0 or 1, in combination with a pharmaceutically acceptable carrier.

52. A method according to claim 51 wherein the compound is of the formula (IV) in the form of a pharmaceutically acceptable di-basic salt.

53. A method according to claim 51 wherein the compound has a single stereochemical form about the double bond.

54. A method according to claim 51 wherein X is bromo.

55. A method according to claim 51 wherein X is chloro.

56. A method according to claim 51 wherein the compound is of the formula (IV) wherein n is 1.

57. A method according to claim 51 wherein n is 0.

58. A method according to claim 51 wherein the compound is in the form of the di-sodium salt.

59. A method according to claim 51 wherein the compound is in the form of the di-potassium salt.

60. A method according to claim 51 wherein the compound is of the formula (IV) in the form of a monobasic pharmaceutically acceptable salt of an in vivo hydrolyzable carboxylate ester.

61. A method according to claim 51 wherein the compound is in the form of the sodium or potassium sulfonate salt of the phthalidyl ester.

62. A method according to claim 51 wherein the compound is in the form of the sodium or potassium salt.

63. A method according to claim 51 wherein the compound is methyl (5R,6R)-3-(2-Acetamido-1-bromoethenylthio)-6-[(1S-1-ethoxysulphonyloxyethyl])-7-oxo-1-azabicyclo[3.2.0.]hept-2-ene-2-carboxylate.

64. A method according to claim 51 wherein the compound is Benzyl (5R, 6R)-3-(2-acetamido-1-bromoethenylthio)-6-[(1S)-1-ethoxysulphonyloxy-ethyl]-7-oxo-1-azabicyclo[3.2.0.]hept-2-ene-2-carboxylate.

65. A method according to claim 51 wherein the compound is p-Nitrobenzyl (5R, 6R)-3-(2-acetamido-1-bromoethenylthio)-6-[benzyldimethyl-n-hexadecylammonium (1S)-1-sulphonatooxyethyl]-7-oxo-1-azabicyclo [3.2.0.]hept-2-ene-2-carboxylate.

66. A method according to claim 51 wherein the compound is p-Nitrobenzyl (5R, 6R)-3-(2-acetamido-1-bromoethenylthio)-6-[sodium-(1S)-1-sulphonatooxyethyl]-7-oxo-1-azabicyclo[3.2.0.]hept-2-ene-2-carboxylate.

67. A method according to claim 51 wherein the compound is Disodium (5R, 6R)-3-(2-acetamido-1-bromoethenylthio)-6-[(1S)-1-sulphonatooxyethyl]-7-oxo-1-azabicyclo [3.2.0.]hept-2-ene-2-carboxylate.

68. A method according to claim 51 wherein the compound is p-bromobenzyl (5R, 6R)-3-(2-acetamido-1-chloroethenylthio)-6-[(1S)-1-ethyloxysulphonyloxyethyl]-7-oxo-1-azabicyclo [3.2.0.]hept-2-ene-2-carboxylate.

69. A method according to claim 51 wherein the compound is Disodium (5R, 6R)-3-(2-acetamido-1-chloroethenylthio)-6-[(1S)-1-sulphonatooxyethyl]-7-oxo-1-azabicyclo [3.2.0.]hept-2-ene-2-carboxylate.

70. A method according to claim 51 wherein the compound is Disodium (5R, 6R)-3-(2-acetamido-1-bromoethenylthio)-6-[(1S)-1-sulphonatooxyethyl]-7-oxo-1-azabicyclo[3.2.0.]hept-2-ene-2-carboxylate.

71. A method according to claim 51 wherein the compound is p-Nitrobenzyl (5R, 6R)-3-(2-acetamido-1-chloroethenylthio)-6-[(1S)-1-ethoxysulphonyloxyethyl]-7-oxo-1-azabicyclo[3.2.0.]hept-2-ene-2-carboxylate.

72. A method according to claim 51 wherein the compound is Methyl (5R,6R)-3-(2-acetamido-1-bromoethenylsulphinyl)-6-[benzyldimethyl-n-hexadecylammonium (1S)-1-sulphonatooxyethyl]-7-oxo-1-azabicyclo[3.2.0.]hept-2-ene-2-carboxylate.

73. A method according to claim 51 wherein the compound is Phthalidyl (5R,6R)-3-(2-acetamido-1-bromoethenylthio) 6 [sodium (1S)-1-sulphonato-oxyethyl]-7-oxo-1-azabicyclo-[3.2.0]hept-2-ene-2-carboxylate.

74. A method according to claim 51 wherein the compound is Disodium (5R,6R)-3-(2-acetamido-1-bromoethenylthio)-6-[(1S)-1-sulphonato-oxyethyl]-7-oxo-1-azabicyclo[3.2.0]hept-2-ene-2-carboxylate.

75. A method according to claim 51 wherein the compound is p-Nitrobenzyl (5R,6R)-3-(2-acetamido-1-bromoethenylthio)-6-[sodium (1S)-1-sulphonato-oxyethyl]-7-oxo-1-azabicyclo[3.2.0]hept-2-ene-2-carboxylate.

76. A method according to claim 51 wherein the administration is oral.

77. A method according to claim 51 wherein the administration is by injection.

* * * * *